(12) United States Patent
Berg et al.

(10) Patent No.: US 8,382,784 B2
(45) Date of Patent: *Feb. 26, 2013

(54) VESSEL CUTTING DEVICES

(75) Inventors: Todd Allen Berg, Stillwater, MN (US); Christopher M. Prigge, New Hope, MN (US)

(73) Assignee: St. Jude Medical ATG, Inc., Maple Grove, MN (US)

(*) Notice: Subject to any disclaimer, the term of this patent is extended or adjusted under 35 U.S.C. 154(b) by 597 days.

This patent is subject to a terminal disclaimer.

(21) Appl. No.: 11/901,550

(22) Filed: Sep. 17, 2007

(65) Prior Publication Data

US 2008/0039882 A1 Feb. 14, 2008

Related U.S. Application Data

(60) Division of application No. 10/456,180, filed on Jun. 6, 2003, now abandoned, which is a continuation of application No. 09/850,021, filed on May 7, 2001, now abandoned, which is a continuation of application No. 09/014,759, filed on Jan. 28, 1998, now Pat. No. 6,416,527.

(51) Int. Cl.
*A61B 17/32* (2006.01)

(52) U.S. Cl. .................................................. 606/180

(58) Field of Classification Search .............. 606/159, 606/167, 170, 180, 184; 604/93.01, 264
See application file for complete search history.

(56) References Cited

U.S. PATENT DOCUMENTS

| | | | |
|---|---|---|---|
| 3,577,979 A | 5/1971 | Van de Gaast | |
| 3,837,345 A | 9/1974 | Matar | |
| 4,007,732 A | 2/1977 | Kvavle et al. | |
| 4,018,228 A | 4/1977 | Goosen | |
| 5,192,294 A | 3/1993 | Blake, III | |
| 5,353,804 A | 10/1994 | Kornberg et al. | |
| 5,403,338 A | 4/1995 | Milo | |
| 5,454,790 A * | 10/1995 | Dubrul | 604/104 |
| 5,488,958 A | 2/1996 | Topel et al. | |
| 5,676,670 A | 10/1997 | Kim | |
| 5,702,412 A | 12/1997 | Popov et al. | |
| 5,824,002 A | 10/1998 | Gentelia et al. | |
| 5,830,222 A | 11/1998 | Makower | |
| 5,972,017 A | 10/1999 | Berg et al. | |
| 5,976,178 A | 11/1999 | Goldsteen et al. | |

(Continued)

FOREIGN PATENT DOCUMENTS

EP 0 807 412 A1 11/1997
WO WO 97/13463 4/1997

(Continued)

*Primary Examiner* — Ryan Severson
*Assistant Examiner* — Ashley Cronin
(74) *Attorney, Agent, or Firm* — Lerner, David, Littenberg, Krumholz & Mentlik, LLP

(57) ABSTRACT

A catheter-based system for accessing specific body cavities percutaneously and minimizing patient trauma is provided. In the preferred embodiment, in order to create an aperture at an access site in a patient's existing tubular body organ structure, a delivery sheath is passed axially along the interior of a portion of the existing tubular body organ structure to place a distal end of the delivery sheath near the access site. A centering wire is passed axially along the interior of the delivery sheath, piercing through from inside to outside of the patient's existing tubular body organ structure at the access site by causing an end portion of the centering wire to emerge from the distal end of the delivery sheath. A cutting catheter is passed substantially coaxially over the centering wire and axially along the interior of the delivery sheath. The aperture is formed by advancing a distal end of the cutting catheter through from inside to outside of the patient's existing tubular body organ structure at the access site and advancing the distal end of the delivery sheath through from inside to outside of the patient's existing tubular body organ structure at the access site.

13 Claims, 5 Drawing Sheets

U.S. PATENT DOCUMENTS

| | | |
|---|---|---|
| 6,001,124 A | 12/1999 | Bachinski |
| 6,030,392 A | 2/2000 | Dakov |
| 6,036,702 A | 3/2000 | Bachinski et al. |
| 6,068,654 A | 5/2000 | Berg et al. |
| 6,074,416 A | 6/2000 | Berg et al. |
| 6,120,432 A | 9/2000 | Sullivan et al. |
| 6,120,511 A * | 9/2000 | Chan ............................... 606/96 |
| 6,190,353 B1 | 2/2001 | Makower et al. |
| 6,254,618 B1 | 7/2001 | Dakov |
| 2001/0039425 A1 | 11/2001 | Dakov |

FOREIGN PATENT DOCUMENTS

| | | |
|---|---|---|
| WO | WO 98/55027 | 12/1998 |
| WO | WO 02/47532 | 6/2002 |

* cited by examiner

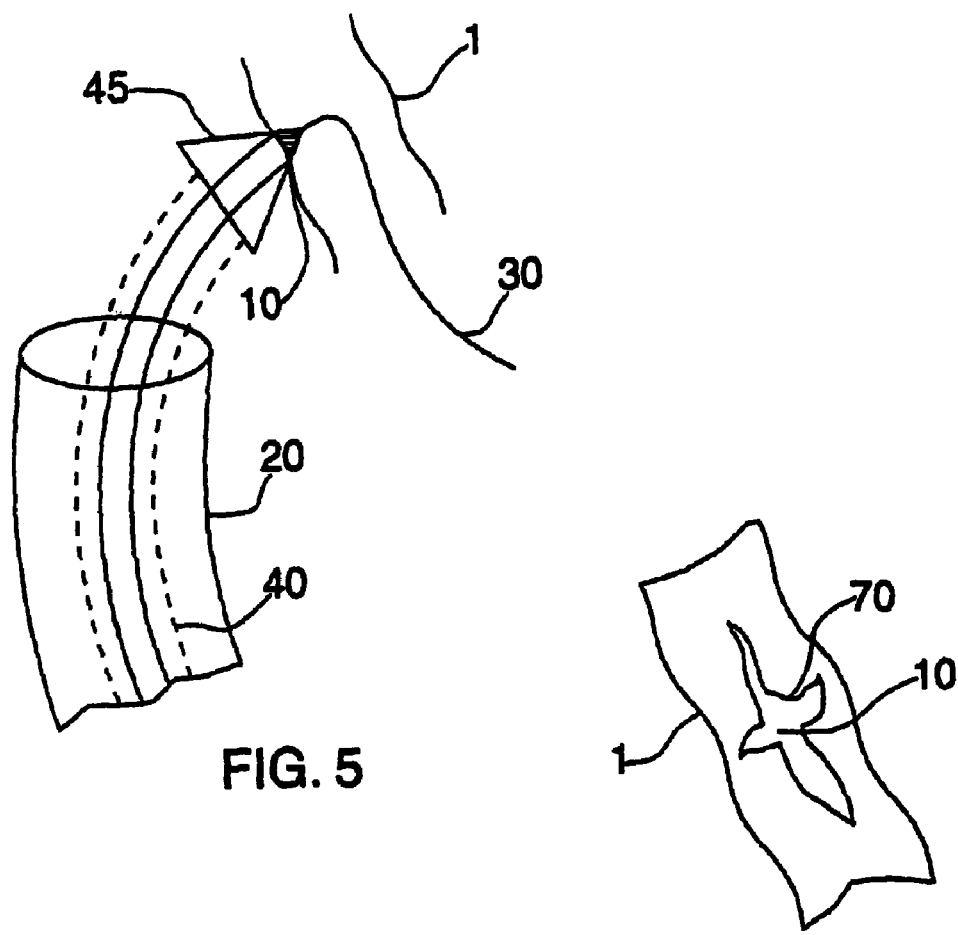
FIG. 5
FIG. 6
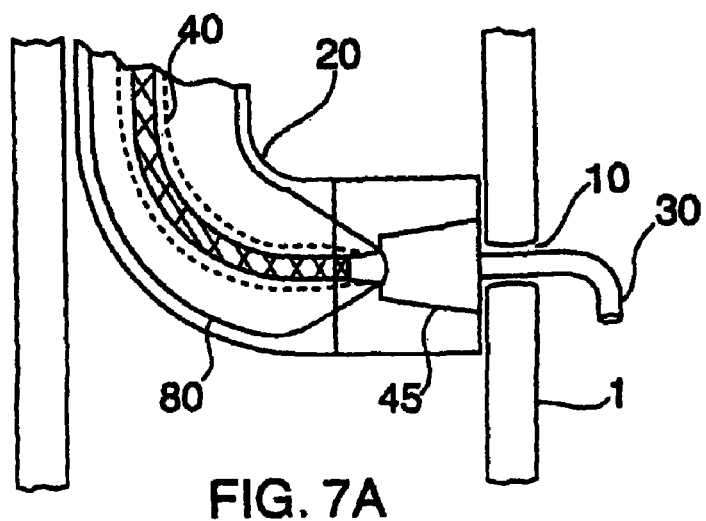
FIG. 7A

VESSEL CUTTING DEVICES

This application is a divisional of U.S. patent application Ser. No. 10/456,180, filed Jun. 6, 2003, which is a continuation of U.S. patent application Ser. No. 09/850,021, filed May 7, 2001 (abandoned), which is a continuation of U.S. patent application Ser. No. 09/014,759, filed Jan. 28, 1998 (now U.S. Pat. No. 6,416,527). These prior applications are hereby incorporated by reference herein in their entireties.

BACKGROUND OF THE INVENTION

This invention relates to vessel cutting devices for use in the repair, replacement, or supplement of a medical patient's natural body organ structures or tissues. More particularly, this invention relates to vessel cutting devices for use in vascular anastomosis (the surgical connection of vessels).

An example of the possible uses of the invention is a minimally invasive cardiac bypass procedure. This and other examples are considered in detail in Goldsteen et al. U.S. Pat. No. 5,976,178, which is hereby incorporated by reference herein in its entirety.

Vascular anastomosis is a delicate and time-consuming procedure in which fast and accurate vessel cutting plays a particularly important role.

In view of the foregoing, it would be desirable to provide a catheter-based system for accessing specific body cavities percutaneously, thereby minimizing patient trauma.

It would also be desirable to provide fast and accurate vessel cutting devices.

SUMMARY OF THE INVENTION

It is an object of the present invention to provide a catheter-based system for accessing specific body cavities percutaneously, thereby minimizing patient trauma. It is also an object to provide fast and accurate vessel cutting devices.

These and other objects are accomplished by providing a method and apparatus for creating an aperture at an access site in a patient's existing tubular body organ structure by passing a delivery sheath axially along the interior of a portion of the existing tubular body organ structure to place a distal end of the delivery sheath near the access site, passing a centering wire axially along the interior of the delivery sheath, piercing through from inside to outside of the patient's existing tubular body organ structure at the access site by causing an end portion of the centering wire to emerge from the distal end of the delivery sheath, passing a cutting catheter substantially coaxially over the centering wire and axially along the interior of the delivery sheath, forming the aperture by advancing a distal end of the cutting catheter through from inside to outside of the patient's existing tubular body organ structure at the access site and advancing the distal end of the delivery sheath through from inside to outside of the patient's existing tubular body organ structure at the access site.

In one embodiment, the distal end of the cutting catheter is rotated to cut through the patient's existing tubular body organ structure at the access site. In another embodiment, a cutting catheter with a conical (preferably star-shaped) cutting edge is pushed through the patient's existing tubular body organ structure at the access site.

The present invention can also be used to create an aperture in the patient's existing tubular body organ structure by advancing a distal end of the cutting catheter through from outside to inside of the patient's existing tubular body organ structure at the access site.

In the most preferred embodiment, all or substantially all necessary apparatus is inserted into the patient via the patient's existing body organ vessel. In addition, all or substantially all apparatus functions are controlled by the physician (a term used herein to also include supporting technicians) from outside the patient's body.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 5 is a simplified elevational view, partly in section, showing the distal end of the cutting catheter advancing through from outside to inside to create an aperture in the patient's existing tubular body organ structure;

FIG. 6 is a side view of the patient's existing tubular body organ structure of FIG. 5, showing the aperture created;

FIG. 7a is still another view similar to FIG. 1a showing the distal end of a delivery sheath in the interior of a portion of the existing tubular body organ structure with a centering wire piercing through from inside to outside of the patient's existing tubular body organ structure at the access site, wherein the cutting catheter includes a dilator;

DETAILED DESCRIPTION OF THE INVENTION

Figure 1A:
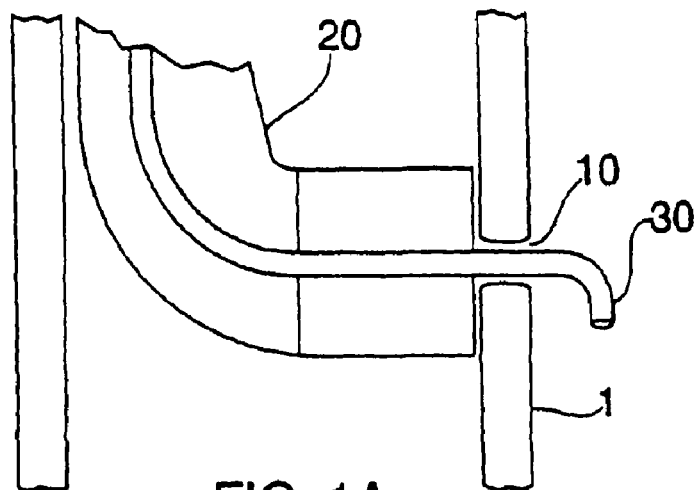
FIG. 1a is a simplified sectional view showing the distal end of a delivery sheath in the interior of a portion of the existing tubular body organ structure with a centering wire piercing through from inside to outside of the patient's existing tubular body organ structure at the access site.

As a preliminary step in creating an aperture at an access site 10 in a patient's existing tubular body organ structure 1, a delivery sheath 20 is passed axially along the interior of a portion of tubular body organ structure 1 to place a distal end of delivery sheath 20 near access site 10. When the distal end of delivery sheath 20 is adjacent to access site 10, a centering wire 30 is passed axially along the interior of the sheath until the end portion of centering wire 30 emerges from the distal end of the sheath and pokes through from inside to outside of tubular body organ structure 1. Centering wire 30 provides a pilot track for cutting catheter 40 to follow. FIG. 1a shows the distal end of delivery sheath 20 in the interior of a portion of tubular body organ structure 1 with a centering wire 30 piercing through from inside to outside of the organ structure at access site 10.

Figure 1B:
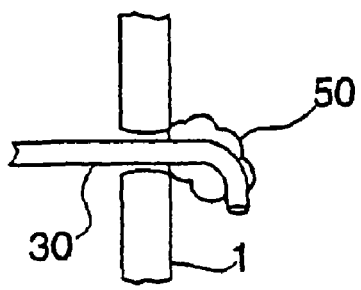
FIG. 1b is a view similar to portions of FIG. 1a showing a centering wire piercing through from inside to outside of the patient's existing tubular body organ structure at the access site, wherein the end portion of the centering wire includes a selectively enlargeable structure.
Figure 1C:
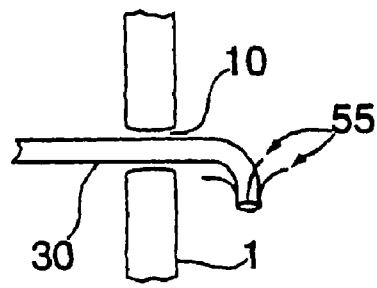
FIG. 1c is another view similar to portions of FIG. 1a showing a centering wire piercing through from inside to outside of the patient's existing tubular body organ structure at the access site, wherein the end portion of the centering wire includes fasteners.

The distal end of centering wire 30 is preferably deformable to facilitate deployment and removal, but resumes its operational (preferably hooked) shape once deployed. Centering wire 30 is kept relatively straight when it is inside sheath 20. But, when centering wire 30 is pushed axially out the distal end of sheath 20, it curves to one side, as shown in FIGS. 1a, 1b and 1c. FIGS. 1b and 1c show alternative structures for centering wire 30. In FIG. 1b, the end portion of centering wire 30 includes a selectively enlargeable structure (such as a balloon 50 which extends annularly around the exterior of the centering wire and projects radially outwardly from the centering wire in all radially outward directions when inflated). In FIG. 1c, the end portion of centering wire 30 includes struts 55 spaced circumferentially around centering wire 30 and which are resiliently biased to project from the centering wire after the end portion of the centering wire pierces through body organ structure 1 at access site 10. By providing a selectively enlargeable structure disposed on the exterior of the centering wire at a predetermined distance proximally from the distal end of the centering wire and enlarging that structure after the centering wire has pierced organ structure 1, it is possible to prevent the portion of centering wire 30 which is distal of the enlargeable structure from passing back into the organ structure. In addition to the retaining function, the enlargeable structure serves to seal the aperture and displace tissue from around the outside of organ structure 1 near access site 10, thereby creating a space. Such a space helps to prevent cutting head 45 from cutting other tissues after exiting organ structure 1 at access site 10.

Figure 2:
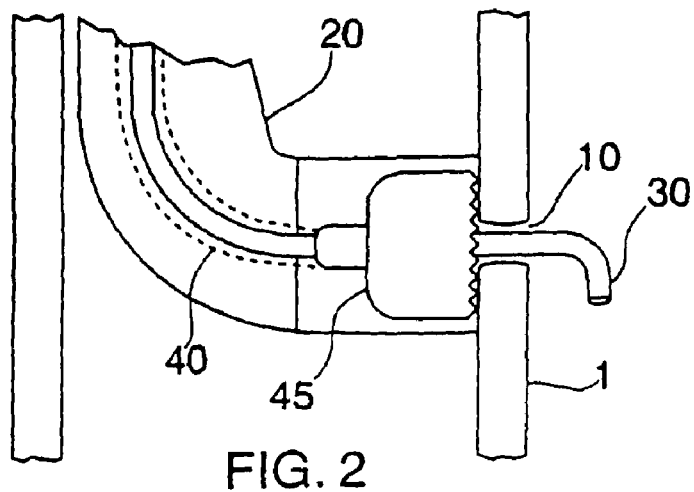
FIG. 2 is yet another view similar to FIG. 1a showing a cutting catheter positioned for cutting at the distal end of a delivery sheath at the access site.

After piercing through organ structure 1 at access site 10 with centering wire 30, cutting catheter 40 is passed substantially coaxially over the centering wire and axially along the interior of sheath 20. FIG. 2 shows cutting head 45 of cutting catheter 40 positioned for cutting at the distal end of delivery sheath 20 at access site 10.

Figure 3:
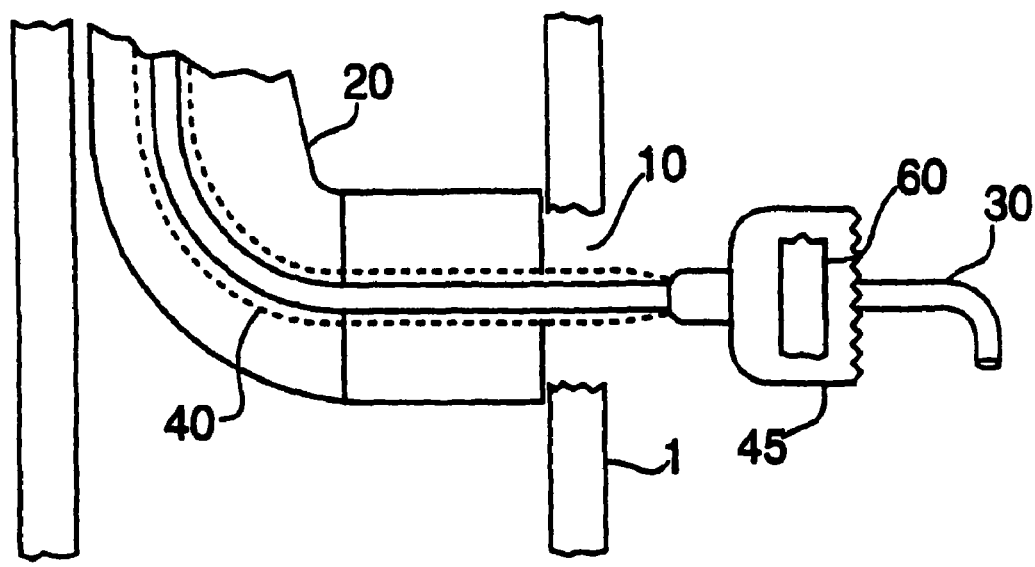
FIG. 3 is still another view similar to FIG. 1a showing forming the aperture by advancing a distal end of the cutting catheter through from inside to outside of the patient's existing tubular body organ structure at the access site.

Centering wire 30 holds cutting catheter 40 and delivery sheath 20 against organ structure 1 at access site 10, thereby preventing undue bleeding during and after the creation of the aperture that could occur if the cutting catheter and the delivery sheath were to move away from the access site. FIG. 3 shows how the aperture is formed by advancing the distal end of cutting catheter 40 (i.e., cutting head 45) through from inside to outside of organ structure 1 at access site 10 by rotating and/or pushing the distal end of the cutting catheter.

Figure 4:
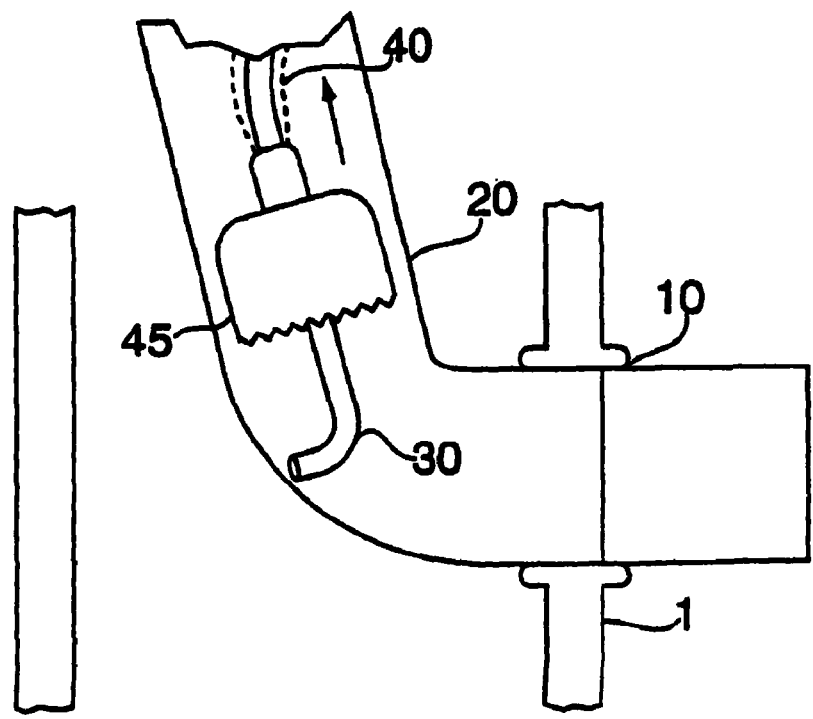
FIG. 4 is yet another view similar to FIG. 1a showing advancing the distal end of the delivery sheath through from inside to outside of the patient's existing tubular body organ structure at the access site.

As shown in FIGS. 2, 3, and 4, the distal end of cutting catheter 40 has a circular cutting edge. Cutting catheter 40, which when advanced by rotation, cuts through tissue and removes tissue plug 60. The preferred embodiment of cutting head 45 also includes a serrated cutting edge and an axially aligned recess for accepting tissue plug 60. By removing plug 60 of tissue (rather than merely displacing tissue, as in FIGS. 5 and 6), the elastic recoil of organ structure 1 at access site 10 is reduced, which may be a desirable condition for optimal graft attachment.

FIG. 4 shows advancing the distal end of delivery sheath 20 through from inside to outside of organ structure 1 at access site 10 and removing centering wire 30 and cutting catheter 40 along with tissue plug 60 contained within cutting head 45.

As shown in FIG. 5, non-rotating cutting catheter 40 can be used to create specific geometric aperture shapes (e.g., oblong aperture 70 for coronary anastomosis). FIG. 5 also shows the use of the present invention in creating an aperture in organ structure 1 by advancing a distal end of cutting catheter 40 through from outside to inside of the organ structure at access site 10. Centering wire 30 is tracked through cutting catheter 40 and is shown piercing organ structure 1 at access site 10. Following such an outside-to-inside aperture, delivery sheath 20 can be passed axially along the interior of a portion of organ structure 1 to place a distal end of delivery sheath 20 near second access site 10 where an inside-to-outside aperture can be created. (Note that organ structure 1 is shown smaller in scale relative to sheath 20 and cutting catheter 40.) FIG. 6 is a side view of organ structure 1, showing aperture 70 created using non-rotating cutting catheter. 40 of FIG. 5.

Figure 7B:
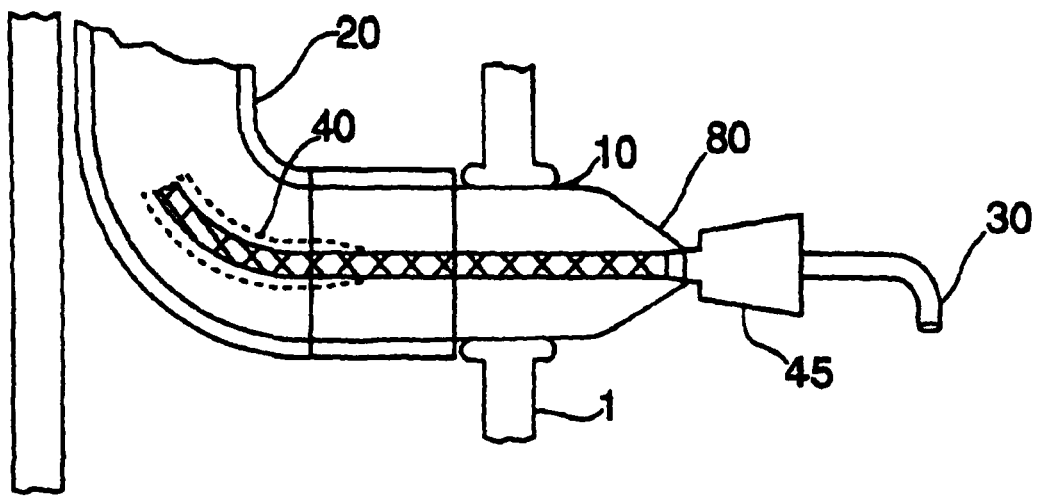
FIG. 7b is yet another view similar to FIG. 1a forming the aperture by advancing a distal end of the cutting catheter through from inside to outside of the patient's existing tubular body organ structure at the access site, wherein the cutting catheter includes a dilator.
Figure 7C:
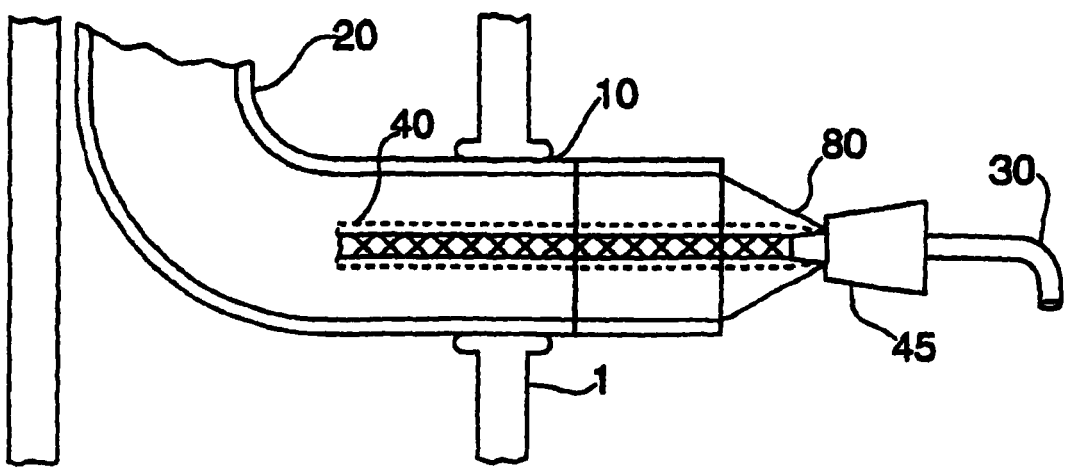
FIG. 7c is still another view similar to FIG. 1a showing advancing the delivery sheath through the aperture at the access site.

Cutting catheter 40 shown in FIG. 7a is a rotating catheter. Cutting head 45 could be a saw-tooth or a razor-edge type, for example. The distal end of delivery sheath 20 is shown in the interior of a portion of organ structure 1 with centering wire 30 piercing through from inside to outside of the organ structure at access site 10, wherein cutting catheter 40 includes dilator 80. Dilator 80 facilitates advancing sheath 20 through the aperture (as is shown by the succession of steps illustrated by FIGS. 7b and 7c).

The outer diameter of dilator 80 is close to the inner diameter of sheath 20 and is typically larger than the diameter of cutting head 45. As shown in FIG. 7b, as dilator 80 advances through the aperture at access site 10, the aperture is simultaneously sealed against bleeding.

Figure 8:
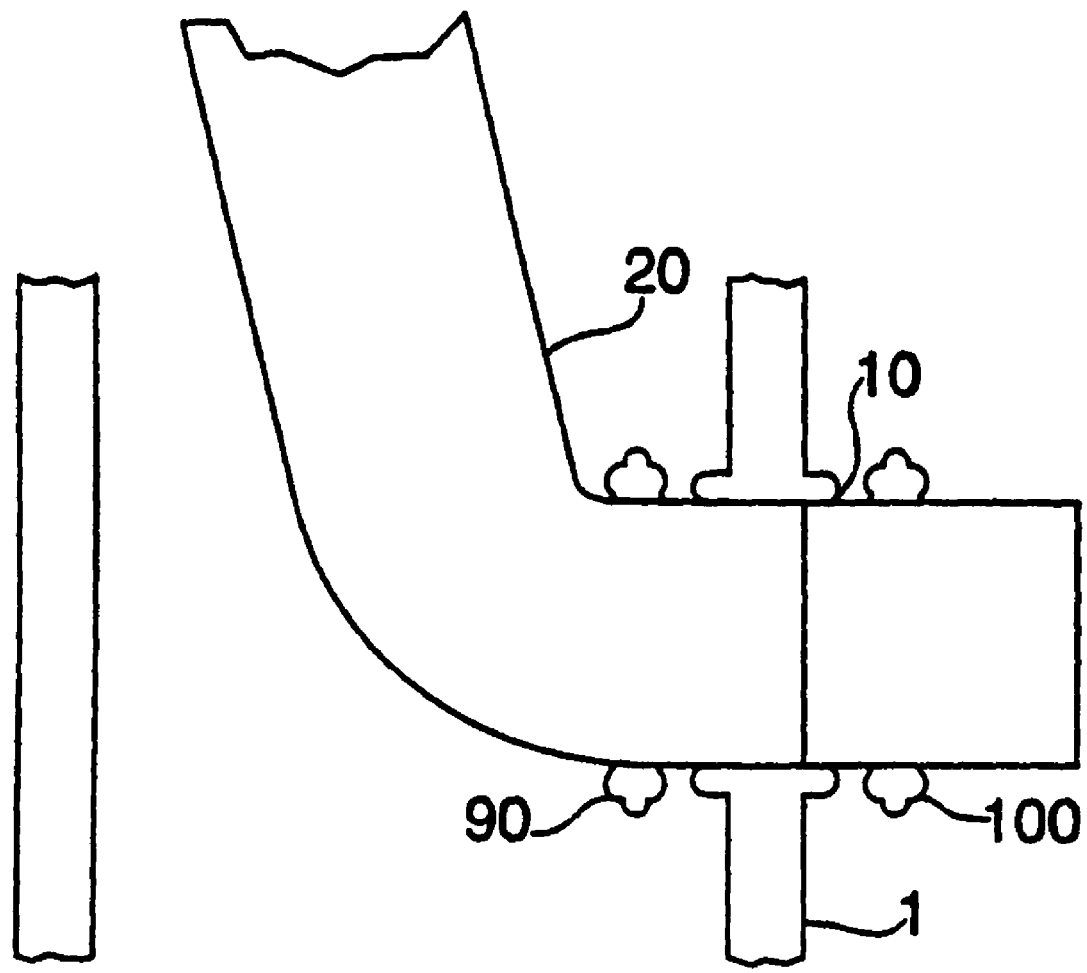
FIG. 8 is yet another view similar to FIG. 1a showing a delivery sheath which includes distal and proximal selectively enlargeable structures.

FIG. 8 shows delivery sheath 20 which includes proximal and distal selectively enlargeable structures 90, 100. Preferably, both selectively enlargeable structures 90 and 100 are balloons which extend annularly around the exterior of delivery sheath 20 and project radially outward when inflated. Although the embodiment shown in FIG. 8 includes both proximal and distal selectively enlargeable structures, either one or both may be included. When enlarged, proximal selectively enlargeable structure 90 prevents more than the portion of delivery sheath 20 which is distal of the enlargeable structure from passing out of the tubular structure via the aperture. Similarly, when enlarged, distal selectively enlargeable structure 100 prevents the portion of delivery sheath 20 which is distal of the enlargeable structure from passing back in to the tubular structure via the aperture.

As an illustrative example of the application of the present invention, consider the following. Delivery sheath 20 (preferably about 4.0 mm in diameter) including cutting catheter 40 is introduced into organ structure 1 percutaneously through the femoral artery near the thigh. Cutting catheter 40 includes cutting head 45 (preferably about 3.5 mm in diameter). Delivery sheath 20 is positioned at access site 10, here the ascending aorta. Centering wire 30 is tracked through cutting catheter 40 and is caused to pierce the aortic artery at access site 10. Cutting catheter 40 is then tracked over centering wire 30 by either pushing or rotating (or a combination of both pushing and rotating) and caused to advance through the aortic wall. An approximately 3.5 mm aperture is created with tissue plug 60 retained in cutting head 45 and removed along with the cutting catheter 40. Delivery sheath 20 can now be advanced through the approximately 3.5 mm aperture created by the cutting catheter 40, causing organ structure 1 to stretch slightly (i.e., about 0.5 mm). This stretching is desirable because it provides a blood seal around delivery sheath 20 to prevent bleeding into the chest cavity. Delivery sheath 20 can now be used to introduce other catheters (including cameras, for example) from the femoral artery into the chest cavity for the purpose of diagnosis or intervention (e.g., grafts or TMR laser surgery).

To minimize patient trauma, delivery sheath 20, cutting catheter 40, and centering wire 30 are all preferably coupled to and controlled by a controller located on the outside of the patient.

Various methods and apparatus for delivering and installing plugs in walls of organ structures, as well as methods and apparatus for promoting the closing and healing of apertures in walls of organ structures, are available (e.g., of the type shown in Goldsteen et al. U.S. Pat. No. 5,976,178; published PCT patent application WO 98/47430; and published PCT patent application WO 98/55027, all of which are hereby incorporated by reference herein).

Thus, it is seen that a method and apparatus for creating an aperture at an access site in a patient's existing tubular body organ structure and making it possible to access specific body cavities percutaneously, thereby minimizing patient trauma, is provided. One skilled in the art will appreciate that the present invention can be practiced by other than the described embodiments, which are presented for purposes of illustration and not of limitation, and the present invention is limited only by the claims which follow.

What is claimed is:

1. Instrumentation for facilitating cutting an opening in a side wall of a body conduit comprising:
    a tubular structure defining a lumen and having a sharpened distal end portion configured to cut a section of the body conduit to create the opening; and
    a tissue holding structure axially movable within the lumen of the tubular structure, the tissue holding structure comprising a piercing portion operable to form an aperture in the body conduit to permit passage of the tissue holding structure through the body conduit from an entrance side adjacent the tubular structure to an exit side thereof, and a centering guide wire extending through the tubular structure, the centering guide wire including a distal end portion having a substantially linear first configuration when entirely within the tubular structure, the distal end portion biased to have a curved second configuration when the distal end portion extends out from the tubular structure, the distal end portion having a retention member affixed thereon to secure the section of the body conduit to the tissue holding structure during movement of the tissue holding structure to approximate the entrance side of the section of the body conduit and the sharpened distal portion of the tubular structure which cuts the section of body conduit.

2. The instrumentation as defined in claim 1, wherein the tissue holding structure and the section of body conduit secured thereto by the retention member are movable into the lumen of the tubular structure.

3. The instrumentation as defined in claim 1, wherein the aperture formed by the piercing portion has a first cross-sectional size, and the retention member is resiliently biased radially outwardly to a second cross-sectional size greater than the first cross-sectional size in order to secure the section of body conduit and to seal the aperture in the body conduit.

4. The instrumentation as defined in claim 3, wherein the retention member is a balloon, and the balloon is deflected radially inwardly during the distal passage of the tissue holding structure through the section of the body conduit.

5. The instrumentation as defined in claim 1, wherein the sharpened distal end portion of the tubular structure is configured to cut the section of body conduit by axial rotation of the tubular structure.

6. The instrumentation as defined in claim 1, wherein the sharpened distal end portion of the tubular structure is configured to cut the section of body conduit by longitudinal advancement of the tubular structure through the body conduit.

7. The instrumentation as defined in claim 1 wherein the centering guide wire is shaped to pierce through the side wall of the body conduit to form an opening through which the retention member passes and the retention member when resiliently biased radially outwardly prevents the distal end of the centering guide wire from passing back though the opening of the body conduit.

8. The instrumentation as defined in claim 3, wherein the retention member is a balloon that is configured to secure the section of the body conduit to the tissue holding structure while the entire balloon is located only on the exit side of the body conduit.

9. The instrumentation as defined in claim 1, wherein the retention member is a strut that is resiliently biased outwardly in order to secure the section of body conduit.

10. The instrumentation as defined in claim 9, wherein the strut is deflected inwardly during the distal passage of the tissue holding structure through the section of the body conduit.

11. The instrumentation as defined in claim 1, wherein the retention member is a plurality of struts that are spaced circumferentially around the centering guide wire and are resiliently biased outwardly in order to secure the section of body conduit.

12. The instrumentation as defined in claim 11, wherein the plurality of struts extend outwardly from a distal tip of the centering guide wire.

13. The instrumentation as defined in claim 1, further comprising a dilator positioned substantially coaxially over the centering guide wire, the dilator configured to facilitate advancing of the tubular structure through the opening in the body conduit.

* * * * *